US008960905B2

(12) United States Patent
Aoki et al.

(10) Patent No.: US 8,960,905 B2
(45) Date of Patent: Feb. 24, 2015

(54) OPTICAL TOMOGRAPHIC APPARATUS AND CONTROL METHOD THEREOF

(75) Inventors: Hiroshi Aoki, Saitama (JP); Hirofumi Yoshida, Yokohama (JP); Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 165 days.

(21) Appl. No.: 13/598,789

(22) Filed: Aug. 30, 2012

(65) Prior Publication Data
US 2013/0194542 A1 Aug. 1, 2013

(30) Foreign Application Priority Data

Jan. 26, 2012 (JP) ................................. 2012-014649

(51) Int. Cl.
*A61B 3/14* (2006.01)
(52) U.S. Cl.
USPC .......................................... 351/206; 351/246
(58) Field of Classification Search
USPC .................... 351/206, 221, 246, 205
See application file for complete search history.

(56) References Cited

U.S. PATENT DOCUMENTS

| | | | |
|---|---|---|---|
| 5,144,346 A | 9/1992 | Nakamura et al. |
| 5,751,396 A | 5/1998 | Masuda et al. |
| 7,400,410 B2 | 7/2008 | Baker et al. |
| 7,480,059 B2 | 1/2009 | Zhou et al. |
| 7,830,525 B2 | 11/2010 | Buckland et al. |
| 7,999,947 B2 | 8/2011 | Buckland et al. |
| 8,085,408 B2 | 12/2011 | Everett et al. |
| 8,120,779 B2 | 2/2012 | Buckland et al. |
| 8,251,510 B2 | 8/2012 | Kobayashi et al. |
| 8,274,660 B2 | 9/2012 | Sugita |
| 8,294,901 B2 | 10/2012 | Yoshida et al. |
| 8,308,297 B2 | 11/2012 | Hirose et al. |
| 8,419,186 B2 | 4/2013 | Isogai et al. |
| 8,427,654 B2 | 4/2013 | Horn et al. |
| 8,749,795 B2 | 6/2014 | Sugita |
| 8,818,063 B2 | 8/2014 | Suehira |
| 2007/0076217 A1 | 4/2007 | Baker et al. |
| 2007/0291277 A1 | 12/2007 | Everett et al. |

(Continued)

FOREIGN PATENT DOCUMENTS

| | | |
|---|---|---|
| CN | 101791213 A | 8/2010 |
| CN | 101822530 A | 9/2010 |

(Continued)

OTHER PUBLICATIONS

May 14, 2013 European Search Report in European Patent Appln. No. 13152801.0.

(Continued)

*Primary Examiner* — Hung Dang
(74) *Attorney, Agent, or Firm* — Fitzpatrick, Cella, Harper & Scinto

(57) ABSTRACT

In order to change a size of an imaging area of a tomographic image of an object to be inspected easily, provided is an optical tomographic apparatus for acquiring a tomographic image of an object to be inspected, the optical tomographic apparatus including a control unit for controlling a measuring light path length changing unit to change an optical path length of measuring light in a case where the size of the imaging area of the tomographic image is changed, and for controlling a reference light path length changing unit to change an optical path length of reference light in association with the change in the optical path length of the measuring light.

15 Claims, 11 Drawing Sheets

(56) References Cited

U.S. PATENT DOCUMENTS

| | | |
|---|---|---|
| 2008/0106696 A1 | 5/2008 | Buckland et al. |
| 2008/0246918 A1 | 10/2008 | Zhou et al. |
| 2009/0115964 A1* | 5/2009 | Ueno .......................... 351/206 |
| 2009/0141237 A1 | 6/2009 | Izatt et al. |
| 2010/0128960 A1 | 5/2010 | Yumikake |
| 2010/0181462 A1 | 7/2010 | Sugita |
| 2010/0226553 A1 | 9/2010 | Suehira |
| 2010/0238403 A1 | 9/2010 | Kobayashi et al. |
| 2010/0315592 A1 | 12/2010 | Buckland et al. |
| 2010/0321636 A1 | 12/2010 | Buckland et al. |
| 2011/0007321 A1 | 1/2011 | Everett et al. |
| 2011/0102742 A1 | 5/2011 | Miyasa et al. |
| 2011/0130652 A1 | 6/2011 | Boppart et al. |
| 2011/0170062 A1 | 7/2011 | Isogai et al. |
| 2011/0176107 A1 | 7/2011 | Yoshida et al. |
| 2011/0267581 A1 | 11/2011 | Nakajima et al. |
| 2012/0044499 A1 | 2/2012 | Shimoyama et al. |
| 2012/0050678 A1 | 3/2012 | Aoki |
| 2012/0075640 A1 | 3/2012 | Sakagawa et al. |
| 2012/0140176 A1 | 6/2012 | Buckland et al. |
| 2012/0140238 A1 | 6/2012 | Horn et al. |
| 2012/0250029 A1 | 10/2012 | Yoshida |
| 2012/0293807 A1 | 11/2012 | Sugita |

FOREIGN PATENT DOCUMENTS

| | | |
|---|---|---|
| EP | 2233065 A2 | 9/2010 |
| EP | 2382914 A1 | 11/2011 |
| JP | 2002-236090 A | 8/2002 |
| JP | 2009-022502 A | 2/2009 |
| JP | 2009-160190 A | 7/2009 |
| JP | 2009-291252 A | 12/2009 |
| JP | 2011-147609 A | 8/2011 |
| JP | 2011-147612 A | 8/2011 |
| JP | 2011-245183 A | 12/2011 |

OTHER PUBLICATIONS

Aug. 5, 2014 Chinese Official Action in Chinese Patent Appln. No. 201310033007.9.

* cited by examiner

OPTICAL TOMOGRAPHIC APPARATUS AND CONTROL METHOD THEREOF

BACKGROUND OF THE INVENTION

1. Field of the Invention

The present invention relates to an optical tomographic apparatus and a control method thereof. For example, the present invention relates to an optical tomographic apparatus used for ophthalmic care, and a control method thereof.

2. Related Background Art

In recent years, an optical image measurement technology for forming images of a surface and an inside of an object to be measured through use of light has been drawing attention. The optical image measurement technology has no invasiveness to a human body unlike a conventional X-ray CT, and hence, its application to a medical field, in particular, is being expected. Above all, its application to an ophthalmic field is advancing remarkably.

As a typical procedure of the optical image measurement technology, there is a procedure called Optical Coherence Tomography (OCT). According to this procedure, owing to the use of an interferometer, measurement with high resolution and high sensitivity can be performed. There is also an advantage in that safety to a subject is high owing to the use of extremely weak light in a wide band as illumination light.

An optical tomographic apparatus using the Optical Coherence Tomography (OCT) utilizing optical interference (hereinafter referred to as "OCT apparatus") is an apparatus capable of acquiring a tomographic image of a sample with high resolution, and particularly, relates to an anterior ocular segment optical tomographic apparatus for forming an image of an anterior ocular segment of an eye to be inspected.

The OCT apparatus is capable of irradiating a sample with measuring light that is low coherent light and measuring backscattered light from the sample with high sensitivity through use of an interference system or an interference optical system. Further, the OCT apparatus can acquire a tomographic image with high resolution by scanning the sample with the measuring light. Thus, a tomographic image of a cornea site in an anterior ocular segment of an eye to be inspected is acquired and utilized in ophthalmic diagnosis and the like.

In such an ophthalmic apparatus, in order to take an image, an inspection portion (mainly, a measurement optical system) of the apparatus is matched with an anterior ocular segment cornea site of an eye to be inspected and an imaging position of an interference optical system, and the eye to be inspected and the apparatus are aligned at a predetermined length.

Japanese Patent Application Laid-Open No. 2009-22502 describes a cornea observing apparatus capable of grasping a depth position of an image in a cornea and determining an abnormal state of a cell of the cornea. In the cornea observing apparatus, in order to take an image of each site of a cornea epithelium, a Bowman's layer, a corneal stromal layer, a Descemet's layer, or a cornea epidermis of an anterior ocular segment, a reference mirror is moved. Further, a distance between an eye to be inspected and a cornea observing apparatus is set to a predetermined length regarding each photographing site, and the reference mirror is moved to perform actual photographing.

Further, Japanese Patent Application Laid-Open No. 2011-147612 describes an optical tomographic apparatus capable of taking both an anterior ocular segment tomographic image and an eyeground tomographic image. This apparatus is an ophthalmic photographing apparatus that involves moving a reference mirror in an interference optical system to move a photographing position of the interference optical system to a predetermined position in accordance with an anterior ocular segment photographing mode and an eyeground photographing mode. The ophthalmic photographing apparatus has a configuration in which the reference mirror is moved to a predetermined position in an anterior ocular photographing mode, and at that time, a distance between an eye to be inspected and the ophthalmic photographing apparatus is set to a predetermined length.

In this case, when an attempt is made so as to acquire a tomographic image of a desired site in an anterior ocular segment, it is generally necessary to obtain a state in which the desired site is present in a portion corresponding to an imaging position by moving a fixation lamp. In this case, a burden on a subject or difficulty in operation for obtaining the expected state cannot be avoided. Further, as another aspect, it is also conceivable to cleave a desired site from a taken tomographic image and electronically enlarging the site. However, a decrease in resolution involved in enlargement, an increase in time required for enlarging, and the like cannot be avoided.

SUMMARY OF THE INVENTION

In view of the above-mentioned problems, it is an object of the present invention to provide an optical tomographic apparatus capable of easily changing a size of an imaging area of a tomographic image of an object to be inspected and a control method thereof.

The present invention provides an optical tomographic apparatus configured as follows.

That is, the optical tomographic apparatus according to the present invention is an optical tomographic apparatus configured to acquire a tomographic image of an object to be inspected based on light obtained by combining return light from the object to be inspected irradiated with measuring light with reference light corresponding to the measuring light, the optical tomographic apparatus including:

a measuring light path length changing unit configured to change an optical path length of the measuring light;

a reference light path length changing unit configured to change an optical path length of the reference light; and a control unit configured to control the measuring light path length changing unit to change the optical path length of the measuring light in a case where a size of an imaging area of the tomographic image is changed, and configured to control the reference light path length changing unit to change the optical path length of the reference light in association with the change in the optical path length of the measuring light.

Further features of the present invention will become apparent from the following description of exemplary embodiments with reference to the attached drawings.

DETAILED DESCRIPTION OF PREFERRED EMBODIMENT

Preferred embodiments of the present invention will now be described in detail in accordance with the accompanying drawings.

An embodiment of the present invention is hereinafter described.

First Embodiment

An optical tomographic apparatus (OCT apparatus) according to this embodiment is described below.

(Schematic Configuration of Apparatus)

A schematic configuration of the optical tomographic apparatus according to this embodiment is described with reference to FIG. 1.

Figure 1:
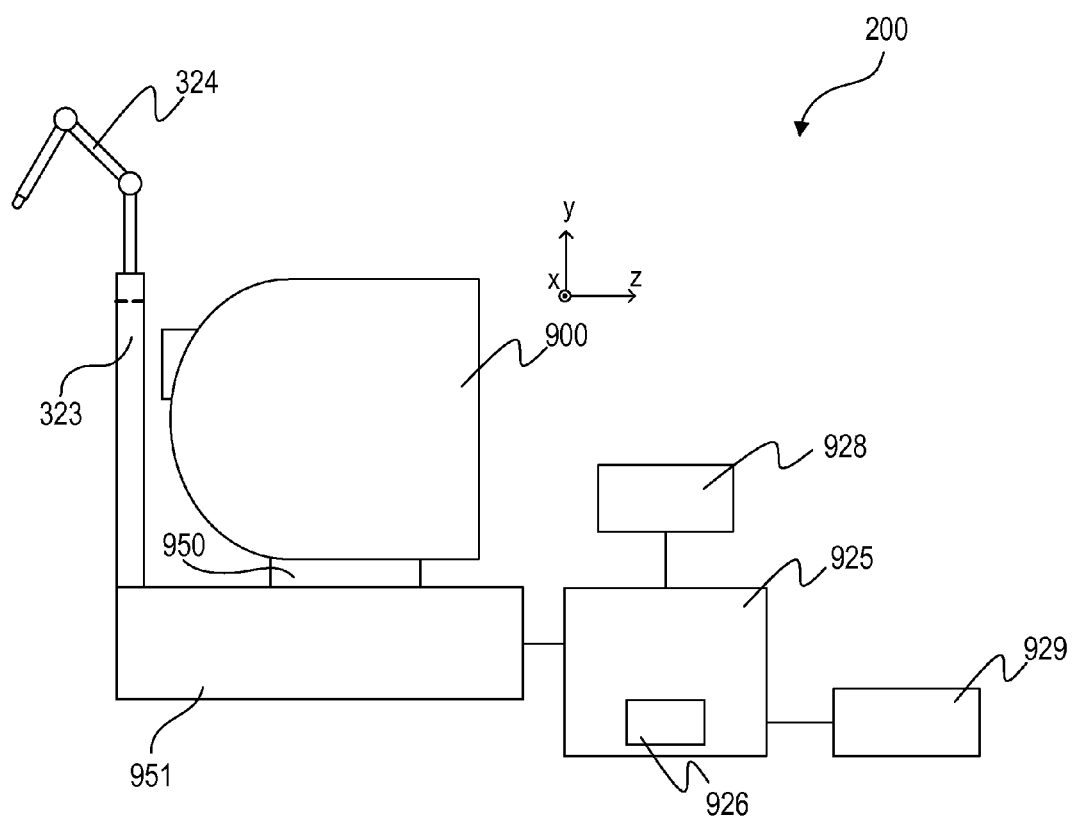
FIG. 1 is a view illustrating an entire apparatus according to an embodiment of the present invention.

FIG. 1 is a side view of an optical tomographic apparatus. An optical tomographic apparatus 200 includes an optical head 900 that is a measurement optical system for taking a two-dimensional image and a tomographic image of an anterior ocular segment and a stage portion 950 that is a movable portion capable of moving the optical head through use of motors (not shown) in xyz directions. A base portion 951 contains a spectrometer (described later).

A personal computer 925, which also serves as a control portion of the stage portion, controls the stage portion and configures a tomographic image. A hard disk 926 also serves as a subject information storage portion and stores a program for taking a tomographic image. A monitor 928 serves as a display portion, and an input portion 929 gives an instruction to the personal computer. Specifically, the input portion 929 includes a keyboard and a mouse. A jaw holder 323 holds a jaw and a forehead of a subject to urge the subject to fix an eye (eye to be inspected). An external fixation lamp 324 is used for visual fixation of the eye of the subject. The external fixation lamp 324 and an internal fixation lamp (described later) can be switched.

(Configuration of Measurement Optical System and Spectrometer)

Figure 2:
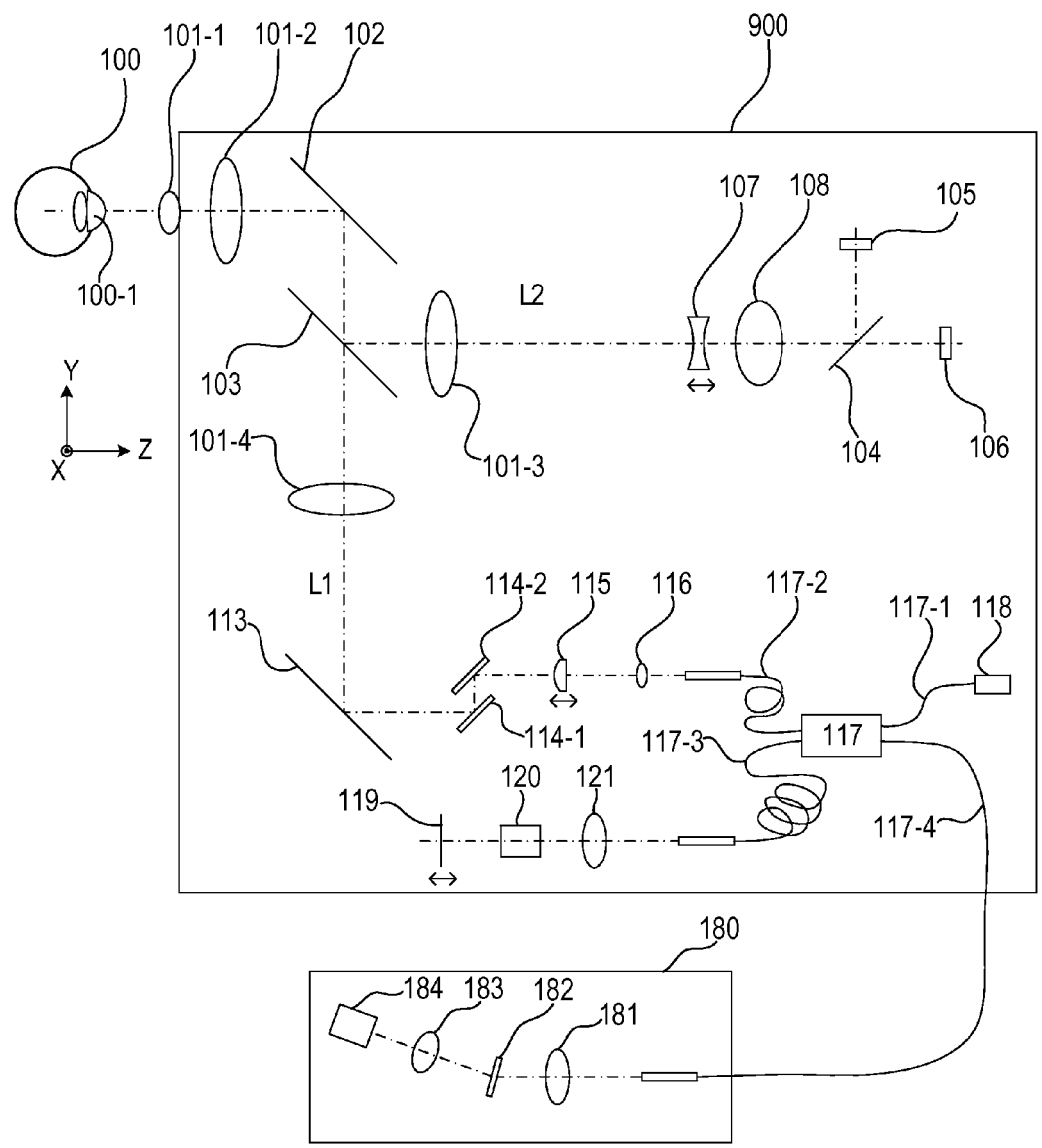
FIG. 2 is a diagram illustrating a measurement optical system configuration according to the embodiment of the present invention.

Configurations of the measurement optical system and the spectrometer of this embodiment are described with reference to FIG. 2.

First, an inside of the optical head 900 is described. Objective lenses 101-1 and 101-2 are set so as to be opposed to an eye to be inspected 100, and an optical path on an optical axis thereof is branched into an optical path L1 of an OCT optical system and an optical path L2 for anterior ocular segment observation and internal fixation lamp depending on the wavelength band by a reflective mirror 102 and a dichroic mirror 103.

The optical path L2 is further branched into an optical path to a CCD 105 for anterior ocular segment observation and an optical path to an internal fixation lamp 106 by a third dichroic mirror 104 depending on the wavelength band in the same way as the above. Here, out of lenses 101-3, 107, and 108, the lens 107 is driven with a motor (not shown) for focus adjustment for fixation lamp and anterior ocular segment observation. The CCD 105 has sensitivity in the vicinity of a wavelength of illumination light for anterior ocular segment observation (not shown), specifically, 780 nm. On the other hand, the internal fixation lamp 106 generates visible light to urge the subject to fix the eye.

The optical path L1 forms the OCT optical system as described above and is used for taking a tomographic image of an anterior ocular segment 100-1 of the eye to be inspected 100. More specifically, the optical path L1 is used for obtaining an interference signal for forming a tomographic image. In the optical path L1, there are arranged a lens 101-4, a mirror 113, and an X-scanner 114-1 and a Y-scanner 114-2 for scanning the anterior ocular segment 100-1 of the eye to be inspected 100 with light. Further, out of lenses 115 and 116, the lens 115 is driven with a motor (not shown) for adjusting focus of light emitted from a light source 118 through a fiber 117-2 connected to an optical coupler 117 onto the anterior ocular segment 100-1. Owing to the focus adjustment, the light from the anterior ocular segment 100-1 simultaneously forms an image in a spot shape to enter an end of the fiber 117-2.

Next, configurations of an optical path from the light source 118, a reference optical system, and the spectrometer are described.

The configurations include the optical source 118, a mirror 119, a dispersion compensation glass 120, the optical coupler 117 described above, optical fibers 117-1 to 117-4 in a single mode connected to the optical coupler 117 to be integrated, a lens 121, and a spectrometer 180.

The above-mentioned components constitute a Michelson interferometer. The light emitted from the light source 118 is split into measuring light on the optical fiber 117-2 side and reference light on the optical fiber 117-3 side through the optical fiber 117-1 via the optical coupler 117. The measuring light illuminates an eyeground of the eye to be inspected 100 to be observed through the optical path of the OCT optical system described above and reaches the optical coupler 117 through the same optical path due to reflection and scattering by a retina.

On the other hand, the reference light reaches the reference mirror 119 through the optical fiber 117-3, the lens 121, and the dispersion compensation glass 120 inserted for matching the dispersion of the measuring light with that of the reference light, and is reflected from the reference mirror 119. Then, the reference light returns through the same optical path and reaches the optical coupler 117. The optical coupler 117 combines the measuring light with the reference light to form interference light. In this case, interference occurs when an optical path length of the measuring light and an optical path length of the reference light satisfy a predetermined condition. The reference mirror 119 is held so as to be adjusted in an optical axis direction by a motor and a drive mechanism (not shown) and is capable of adjusting the optical path length of the reference light to that of the measuring light varying depending on the anterior ocular segment 100-1. The interference light is guided to the spectrometer 180 through the optical fiber 117-4.

The spectrometer 180 includes lenses 181 and 183, a diffraction grating 182, and a line sensor 184. The interference light output from the optical fiber 117-4 is substantially collimated through the lens 181 and dispersed by the diffraction grating 182 to form an image on the line sensor 184 by the lens 183. The line sensor 184 is illustrated as an example of a light receiving element for receiving interference light and generating and outputting an output signal corresponding to the interference light in this embodiment.

Next, the periphery of the light source 118 is described. The light source 118 is a super luminescent diode (SLD) that is a typical low coherent light source. Light emitted from the light source 118 has a central wavelength of 855 nm and a wavelength band width of about 100 nm. In this case, the band width influences a resolution in an optical axis direction of a tomographic image to be acquired, and hence, is an important parameter. Further, although the SLD is selected, the type of the light source 118 is not particularly limited as long as the light source is capable of emitting low coherent light, and amplified spontaneous emission (ASE) or the like may also be used. Considering the measurement of an eye, near-infrared light is suitable for the central wavelength. Further, it is desired that the central wavelength be a shortest possible wavelength because the central wavelength influences a resolution in a lateral direction of a tomographic image to be acquired. For both the reasons, the central wavelength is set to 855 nm.

Although the Michelson interferometer is used as an interferometer in this embodiment, a Mach-Zehnder interferometer may be used. It is desired that the Mach-Zehnder interferometer be used in the case where an optical amount difference between the measuring light and the reference light is large, and the Michelson interferometer be used in the case where the optical amount difference is relatively small.

(Method of Acquiring Tomographic Image)

A method of acquiring a tomographic image through use of the optical tomographic apparatus is described. The optical tomographic apparatus is capable of acquiring a tomographic image in a desired site in the anterior ocular segment 100-1 of the eye to be inspected 100 by controlling the X-scanner 114-1 and the Y-scanner 114-2.

Figure 3:
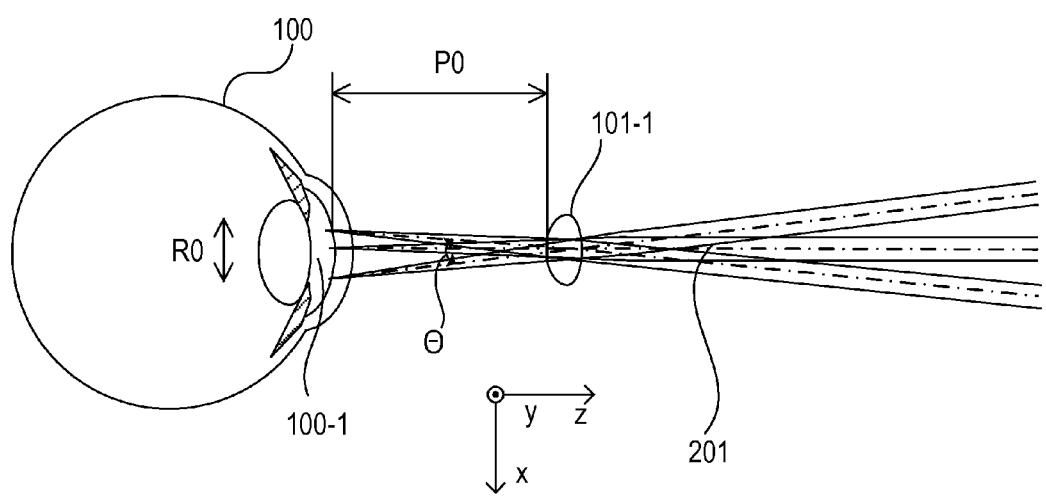
FIG. 3 is an explanatory diagram illustrating a state in which an anterior ocular segment of an eye to be inspected is scanned in an x-direction.

FIG. 3 illustrates a state in which measuring light 201 is radiated to the eye to be inspected 100 to scan the anterior ocular segment 100-1 in the x-direction. The line sensor 184 takes an image based on a predetermined imaging number of pieces of information from an imaging area in the x-direction in the anterior ocular segment 100-1. A luminance distribution on the line sensor 184 obtained at a certain position in the x-direction is subjected to fast Fourier transformation (FFT), and a linear luminance distribution obtained by the FFT is converted into density or color information so as to be displayed on a monitor. This image is referred to as an A scan image. That is, an image is acquired as the A scan image in accordance with an output signal obtained from interference light received by the line sensor 184 that is a light receiving element. A two-dimensional image in which multiple A scan images are arranged is referred to as a B scan image. After acquiring multiple A scan images for constructing one B scan image, a scanning position in the y-direction is moved to perform scanning in the x-direction again to acquire multiple B scan images. By displaying the multiple B scan images or a three-dimensional tomographic image constructed from the multiple B scan images on the monitor, an operator can use those images for diagnosis of the eye to be inspected.

In this case, an angle of view that is an imaging area for acquiring an anterior ocular segment tomographic image is generally determined in accordance with a scan range Ro in the x-direction illustrated in FIGS. 4A to 4C described later. Further, the scan range R0 is determined by a scan angle θ of a scanner and a photographing distance P0 from the objective lens 101-1 to the anterior ocular segment of the eye to be inspected. That is, in the case of changing a size of the imaging region, the scan angle θ or the photographing distance P0 is changed, and the photographing distance P0 can be changed easily by changing the optical path length of the measuring light involving the movement of the optical head 900 in the z-axis direction. Therefore, in this embodiment, the optical head 900 changes the photographing distance P0 by changing the optical path length of the measuring light, and this configuration is defined as a measuring light path length changing unit. Note that, there is another configuration for changing the optical path length of the measuring light than that in this exemplary embodiment, but in this embodiment, the measuring light path length changing unit is defined as a concept including these configurations.

In order to combine the measuring light with the reference light to obtain desired interference, it is required that the optical path length of the measuring light and the optical path length of the reference light move in association with each other so as to satisfy a predetermined condition as described above. Thus, the reference mirror 119 is moved so as to change the optical path length of the reference light in accordance with the optical path length of the measuring light at a position of an anterior ocular segment corresponding to the photographing distance P0.

The reference mirror 119 and a configuration for moving the reference mirror 119 are illustrated as an example of a reference light path length changing unit for changing the optical path length of the reference light in this embodiment. Further, as described above, in order to obtain interference from combined light, it is required that the optical path length of the reference light be changed in accordance with the optical path length of the measuring light. In this embodiment, as an example, a module region functioning as a control unit (sometimes referred to as "optical path length interlocking unit") in the personal computer 925 causes the reference light path length changing unit to change the optical path length of the reference light in association with the change in the optical path length of the measuring light by the measuring light path length changing unit.

Figure 4A:
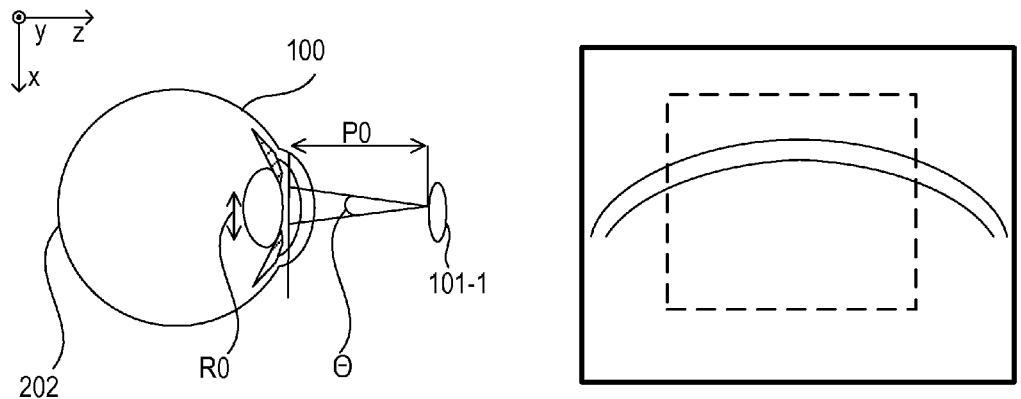
FIGS. 4A, 4B, and 4C are explanatory diagrams each illustrating a scan range at an anterior ocular segment imaging position and an image acquired depending on the scan range.
Figure 4B:
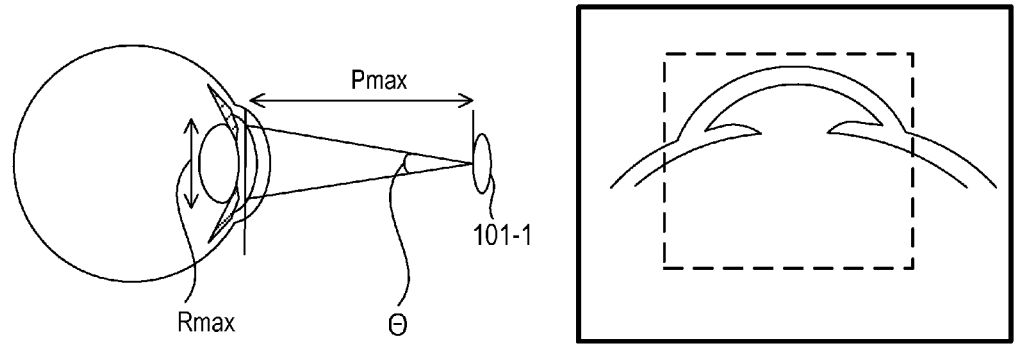
Figure 4C:
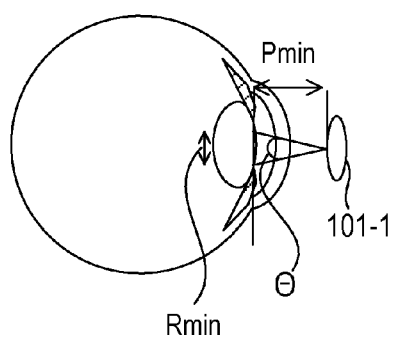
Figure 4C:
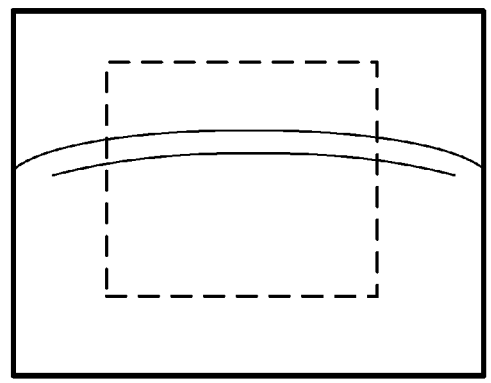

FIGS. 4A to 4C are views illustrating scan ranges at a position of an anterior ocular segment when the photographing distance P0 is changed and illustrating tomographic images displayed in an angle of view at that time, the scan ranges corresponding to the tomographic images. By changing the photographing distance P0 and moving the reference mirror 119 in accordance with this change, a size of an imaging area of the anterior ocular segment can be changed without changing the scan angle θ. By changing the photographing distance P0 to $P_{max}$ so as to increase the distance between an eye to be inspected and the apparatus as illustrated in FIG. 4B and moving the reference mirror 119 to a position corresponding to the photographing distance $P_{max}$, the anterior ocular segment can be taken as an image in a wide scan range $R_{max}$ (angle of view). Further, by changing the photographing distance P0 to $P_{min}$ so as to decrease the distance between the eye to be inspected and the apparatus as illustrated in FIG. 4C and moving the reference mirror 119 to a position corresponding to the photographing distance $P_{min}$, the anterior ocular segment can be taken as an image in a scan range $R_{min}$ that magnifies the anterior ocular segment.

(Measurement Screen)

Figure 5:
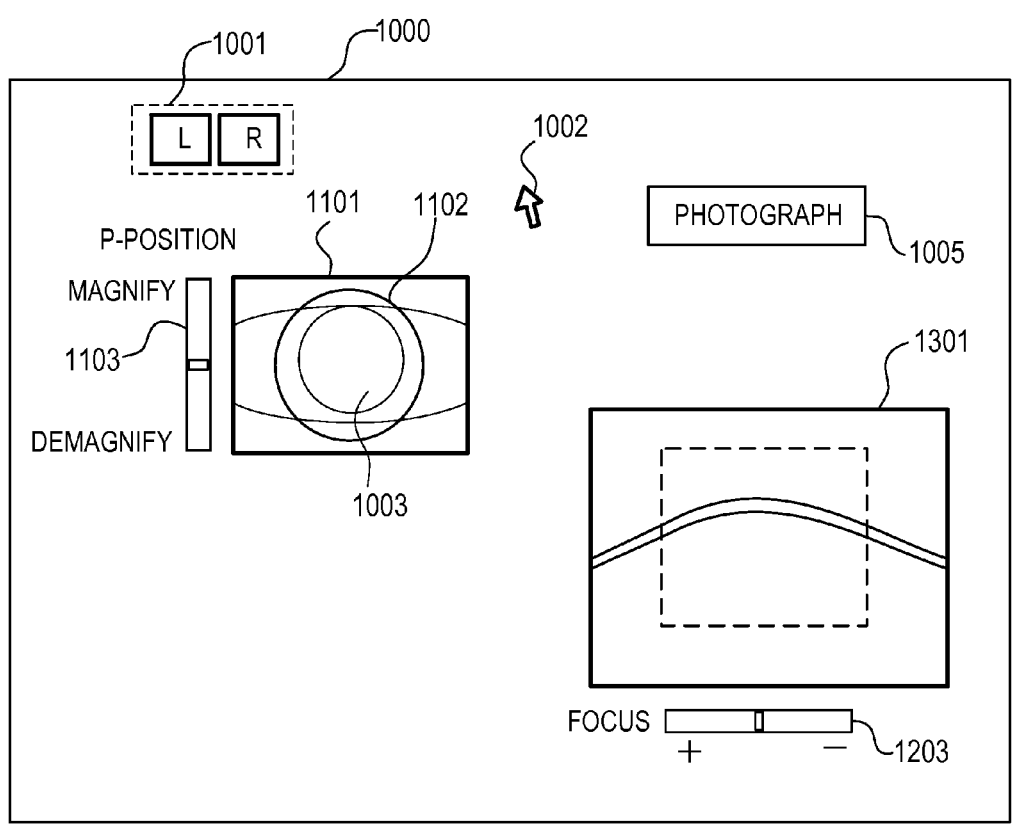
FIG. 5 is a diagram illustrating an example of a measurement operation screen.

FIG. 5 illustrates a measurement screen 1000.

The measurement screen 1000 includes an anterior ocular observation screen 1101 obtained by the CCD 105 for anterior ocular observation, and a tomographic image display screen 1301 for checking an acquired tomographic image.

The optical head 900 is moved to an initial position of a right or left eye by pushing an L or R button 1001 for switching a right eye to be inspected and a left eye to be inspected. The operator operates a mouse included in the input portion 929 to move a position of a mouse cursor 1002. In this measurement apparatus, an alignment unit can be changed in accordance with a position of the mouse cursor by a mouse cursor position detecting unit. The mouse cursor position detecting unit calculates a position of the mouse cursor from a pixel position thereof on the display screen. A range is provided in a measurement screen, and the provided range is associated with alignment drive in advance. Thus, when the mouse cursor is placed in a pixel in the set range, alignment determined in the set range can be performed. Further, an alignment operation by the mouse is performed by rotating a wheel of the mouse.

Further, a slider arranged in the vicinity of each image is used for making adjustment. A slider 1103 designates a photographing distance with respect to an eye to be inspected, and when the slider 1103 is moved, a size of a character 1003 in the anterior ocular observation screen changes in association with the movement of the slider 1103. Further, the size of the character 1003 is associated with the imaging area (angle of view) of the anterior ocular segment, and a change in the character 1003 moves the focus lens 107 for anterior ocular segment observation to a predetermined position. The focus lens 107 is illustrated as an example of an anterior ocular segment observing unit including a focus lens for performing focusing with respect to the anterior ocular segment in this embodiment. An upper limit of the slider corresponds to the anterior ocular segment imaging area $R_{max}$ described above, and a lower limit of the slider corresponds to the anterior ocular segment imaging area $R_{min}$. A slider 1203 performs OCT focus adjustment. The OCT focus adjustment is adjustment for moving the lens 115 in an illustrated direction so as to perform focus adjustment with respect to the anterior ocular segment. Further, these sliders also move in association with an alignment operation by the mouse in each image. That is, independently or in association with the OCT focus adjustment by the slider 1203, a control unit (sometimes referred to as "focus interlocking unit") in the personal computer 925 further causes the OCT focus lens 115 to perform focusing with respect to the anterior ocular segment in association with a change in optical path length of measuring light by the measuring light path length changing unit. It is required that the focus operation with respect to the anterior ocular segment by the anterior ocular segment observing unit be performed in accordance with change in optical path length of measuring light involving a change in photographing distance. In this embodiment, the control unit (sometimes referred to as "focus interlocking unit for an anterior ocular segment") causes the anterior ocular segment observing unit to perform focusing with respect to the anterior ocular segment in association with a change in optical path length of measuring light by the measuring light path length changing unit.

Next, a method of acquiring a tomographic image through use of the OCT apparatus that is a feature of this embodiment, and a method of processing the tomographic image are described with reference to FIGS. 1, 2, and 6. FIG. 7 is a flowchart illustrating an operation of the operator and the personal computer 925.

Anterior ocular segment illumination light (not shown) illuminates the eye to be inspected 100, and thereafter, reflected light therefrom passes through the objective lenses 101-1 and 101-2, and forms an image on the CCD 105 through the optical path L2 described above. The anterior ocular segment image formed on the CCD 105 is read by a CCD control portion (not shown), amplified, subjected to A/D conversion, and input to an operation portion. The anterior ocular image input to the operation portion is taken in the personal computer 925.

Description is hereinafter made with reference to the flowchart of FIG. 7. The personal computer 925 acquires an anterior ocular segment image 1102 in Step S102. In Step S103, with respect to the anterior ocular segment image, when the operator designates a change in a desired imaging area with the slider 1103 described above in the input portion 929 for giving an instruction to the personal computer, the optical head 900 is moved so that a photographing distance corresponding to the imaging area is obtained. In accordance with a change in predetermined length of an optical path length of measuring light involved in the movement of the optical head 900, the reference mirror 119 and the anterior ocular segment focus lens 107 are respectively moved to positions corresponding to the measuring light path length in Step S104. Simultaneously, the anterior ocular segment tomographic image 1301 is acquired by the above-mentioned method of taking a tomographic image. That is, a coherence gate is adjusted so that the anterior ocular segment image 1102 is placed in a photographing frame, and thereafter, in the case where an instruction of a change in photographing area is given, the optical head 900 and the reference mirror 119 are moved in association with each other, with the result that a focus operation is performed. After the operator finishes alignment of the anterior ocular segment and the apparatus in Step S105, the slider 1203 is moved in Step S106. Then, the OCT focus lens 115 is operated, and the operator performs focusing while watching the anterior ocular segment tomographic image 1301 and presses a photographing button 1005 in Step S107 to acquire a tomographic image of the anterior ocular segment. In Step S108, the acquired image is displayed or the image is corrected and displayed. In this case, the image acquired in Step S108 may be an image of a site in a larger range or an image of a site in a smaller range in a screen with the same width, for example, with respect to a tomographic image obtained in the case of the photographing distance P0 that is set as a standard. As described later, the correction is an operation of magnifying or demagnifying a display area (angle of view) so that a site of the photographed images can be displayed with the same size as that of a site obtained at the photographing distance P0. The above-mentioned operation is performed by the module region that functions as an image correcting unit for correcting and changing a display form of an image in the personal computer 925. Further, the display of a cursor or the like for giving an instruction of a change in size of a photographing area on a display unit or the change in display form thereof are performed by the module region that functions as a display control unit included in the control unit.

Figure 8A:
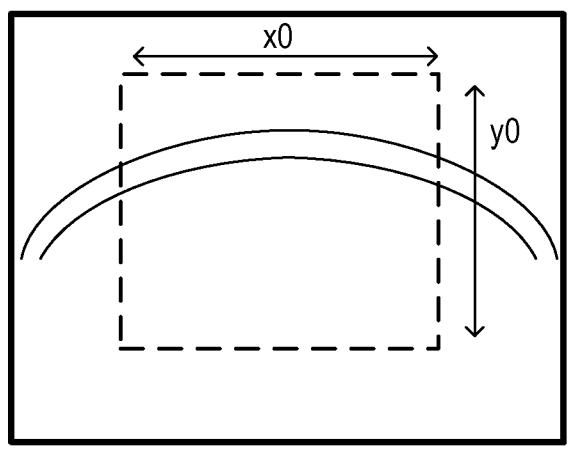
FIGS. 8A, 8B, 8C, 8D, 8E, and 8F are views each illustrating a display example of a tomographic image of an anterior ocular segment and a display example of the corrected tomographic image.
Figure 8B:
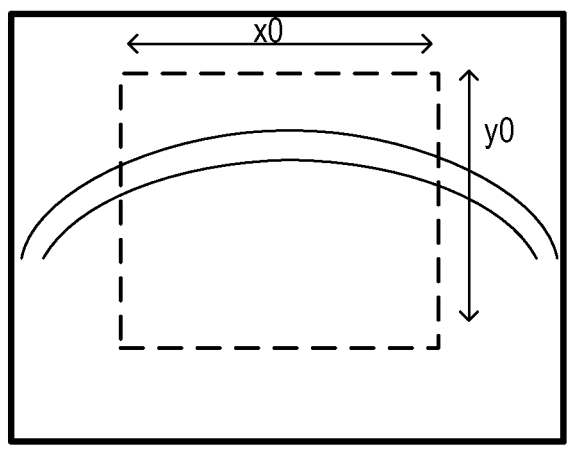
Figure 8C:
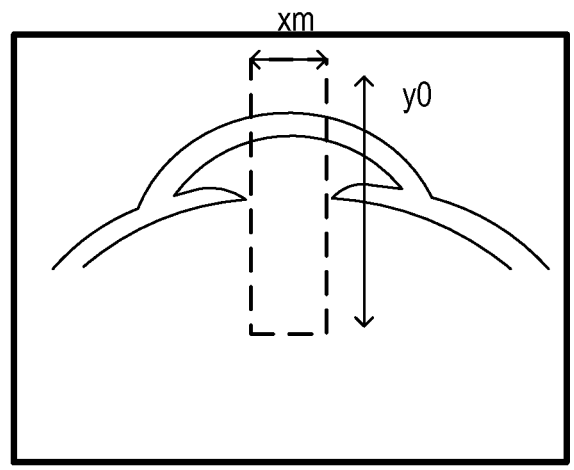
Figure 8D:
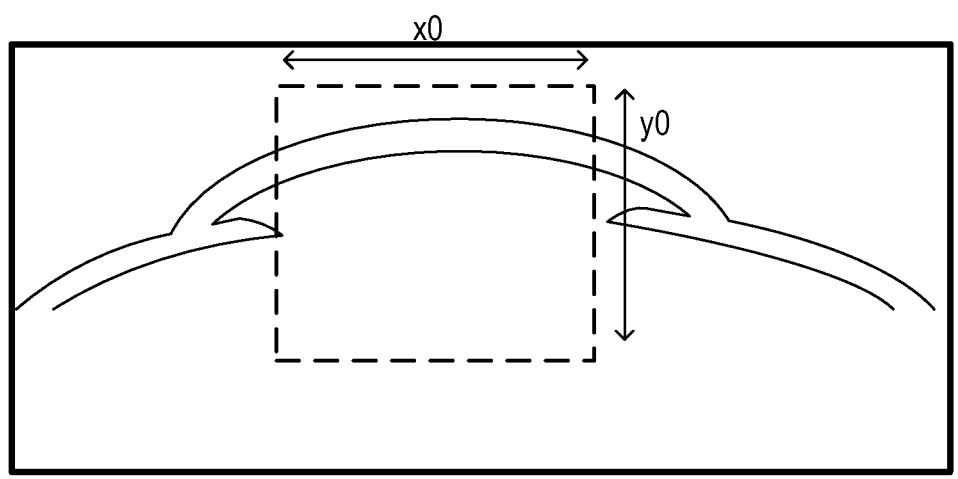
Figure 8E:
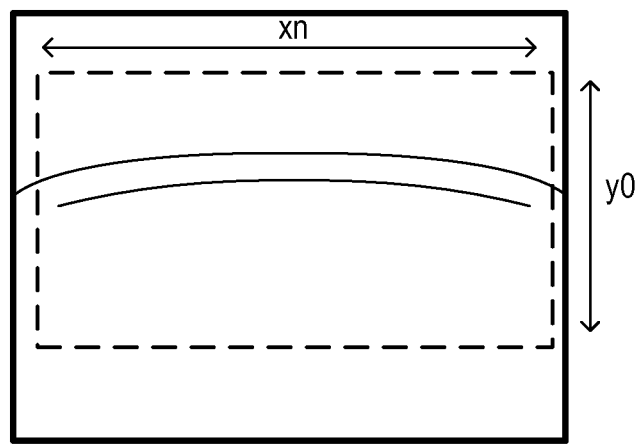
Figure 8F:
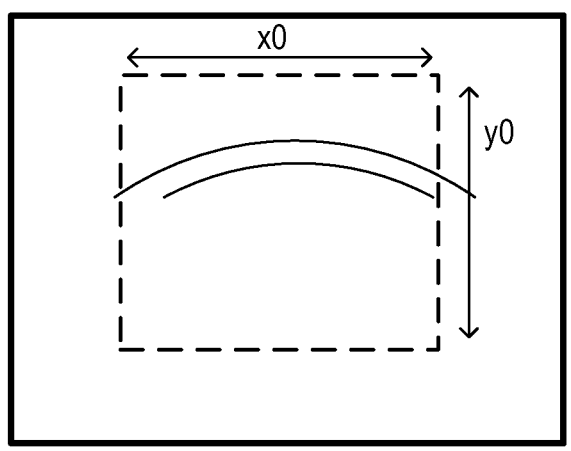

Actually, in the anterior ocular segment tomographic image, only a size in a horizontal direction becomes small without a change in tomographic depth when a photographing distance is larger than a standard distance, and only a size in the horizontal direction becomes large when the photographing distance is smaller than the standard distance. FIGS. 8A to 8F illustrate examples of corrected display images of anterior ocular segment tomographic images. In FIG. 8A, a field of view x0 in the horizontal direction corresponding to the photographing distance P0 becomes narrow to a field of view xm in the horizontal direction as a photographing distance $P_{max}$ increases. Converting the field of view xm into the field of view x0 in the horizontal direction and displaying the field of view x0 as illustrated in FIG. 8D can be easily performed by a known method of processing an image. Regarding the photographing distance $P_{min}$, an image can be processed and displayed as in FIG. 8F. Further, various measurements may be made based on the images of FIGS. 8D and 8F or various measurements may be performed through use of the original figures of FIGS. 8C and 8E by multiplying the photographing distance P by the field of view x in the horizontal direction.

Figure 6:
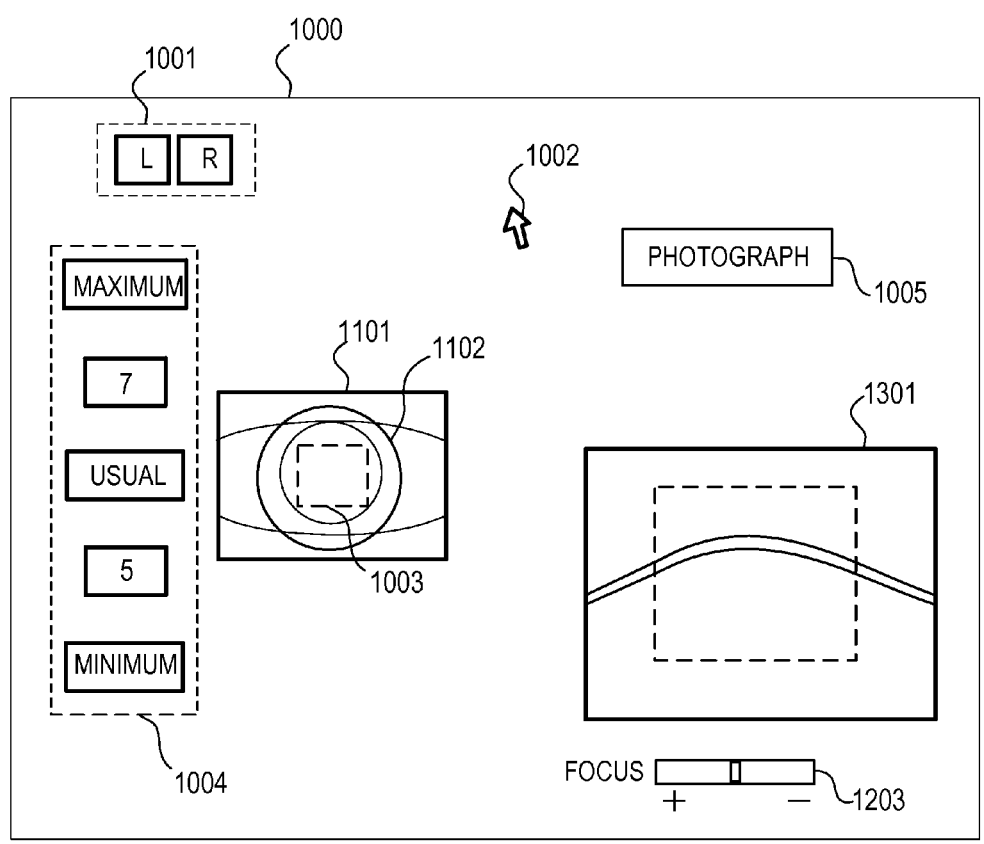
FIG. 6 is a diagram illustrating another example of the measurement operation screen.
Figure 7:
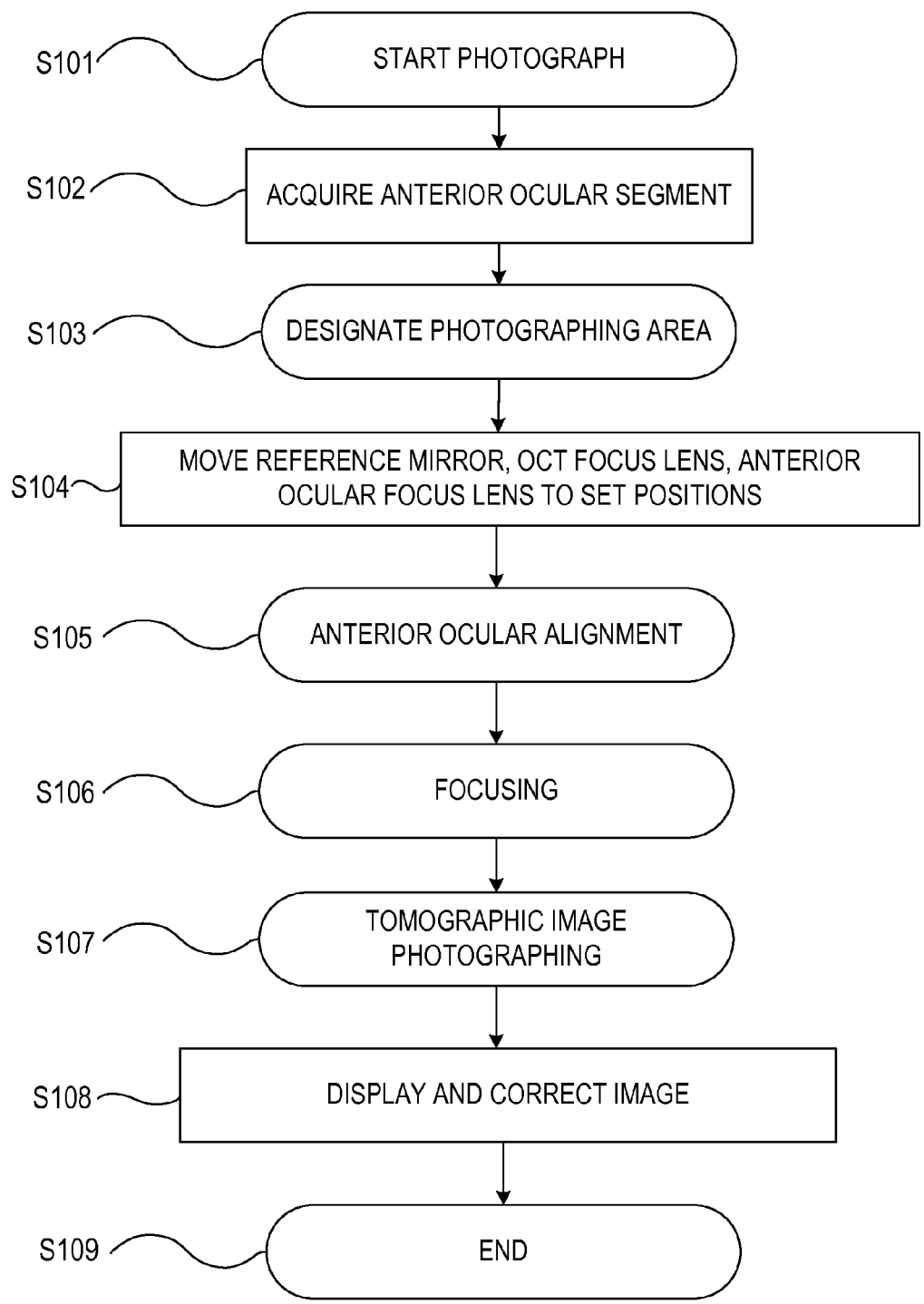
FIG. 7 is a measurement flowchart related to the embodiment of the present invention.

Further, as illustrated in FIG. 6, without acquiring an anterior ocular segment image, an imaging area may be changed without acquiring an anterior ocular segment image through use of an imaging area selection button 1004 instead of the slider 1103. Note that, in FIG. 7, usual (R0=6 mm), maximum ($R_{max}$=9 mm), and minimum ($R_{min}$=3 mm) are respectively set.

Note that, in Step S105, the anterior ocular image taken by the CCD 105 is subjected to image processing to detect a pupil position of the eye to be inspected 100, and thereby, an alignment position relationship between the optical tomographic apparatus and the eye to be inspected 100 can be obtained. This optical tomographic apparatus drives the optical head 900 on an xyz stage (not shown) so that the detected pupil position of the eye to be inspected 100 is placed at an ideal position.

Further, even during photographing of a tomographic image, the anterior ocular segment of the eye to be inspected 100 can always be monitored.

As described above, in the optical tomographic apparatus of this embodiment, an apparatus allowing the operator to designate various imaging areas for photographing can be provided. That is, an optical tomographic apparatus with various fields of view and high resolution can be provided while keeping performance of an optical system. Further, simultaneously, the operation distance between the eye to be inspected and the apparatus can be changed, and hence, the burden on a subject can be alleviated by photographing while setting an operation distance longer in accordance with the state of the subject.

Other Embodiments

Further, this embodiment can also be realized by performing the following processing. That is, the processing involves supplying software (program) for realizing the function of the above-mentioned embodiment to a system or an apparatus via a network or various storage media and causing a computer (or a CPU, an MPU, or the like) of the system or the apparatus to read and execute the program.

Note that, the present invention is not limited to the above-mentioned embodiments and can be variously modified or changed within a scope without departing from the spirit of the embodiments. For example, in the above-mentioned examples, the case where an object to be inspected is an eye has been described, but the embodiments can also be applied to objects to be measured such as a skin and an organ except an eye. In this case, the present invention has an aspect as medical equipment such as an endoscope except an ophthalmic apparatus. Thus, it is preferred that the above-mentioned eye to be inspected be understood as an object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-014649, filed Jan. 26, 2012, which is hereby incorporated by reference herein in its entirety.

What is claimed is:

1. An optical tomographic apparatus configured to acquire a tomographic image of an object to be inspected based on light obtained by combining return light from the object to be inspected irradiated with measuring light with reference light corresponding to the measuring light, the optical tomographic apparatus comprising:
a measuring light path length changing unit configured to change an optical path length of the measuring light;
a reference light path length changing unit configured to change an optical path length of the reference light;
a designating unit configured to designate a size of an imaging area of the tomographic image; and
a control unit configured to control the reference light path length changing unit in association with the measuring light path length changing unit, in accordance with the designation of the designating unit.

2. An optical tomographic apparatus according to claim 1, wherein the control unit controls the reference light path length changing unit in association with the measuring light path length changing unit to change the optical path length of the reference light by a length corresponding to the change in the optical path length of the measuring light, in accordance with the designation of the designating unit.

3. An optical tomographic apparatus according to claim 1, wherein the control unit controls the measuring light path length changing unit to change the optical path length of the measuring light by a length corresponding to a change of the designated size in accordance with the designation of the designating unit, and controls the reference light path length changing unit to change the optical path length of the reference light in association with the change of the optical path length of the measuring light.

4. An optical tomographic apparatus according to claim 1, further comprising a display control unit configured to cause a display unit to display a display form designating the change in the size of the imaging area of the tomographic image, and
wherein the designating unit designates the change in response to an operation of an operation unit.

5. An optical tomographic apparatus according to claim 1, wherein:
the object to be inspected comprises an eye to be inspected; and
the control unit causes the measuring light path length changing unit to change the optical path length of the measuring light by a predetermined length, in a case where a tomographic image of an eyeground of the eye to be inspected is acquired and thereafter a tomographic image of an anterior ocular segment of the eye to be inspected is acquired, and the control unit controls the measuring light path length changing unit, in a case where the optical path length of the measuring light is changed by the predetermined length and thereafter the size of the imaging area of the tomographic image is changed.

6. An optical tomographic apparatus according to claim 1, further comprising an image correcting unit configured to correct the tomographic image in accordance with the optical path length of the measuring light to be determined by the measuring light path length changing unit.

7. An optical tomographic apparatus according to claim 1, wherein:
the object to be inspected comprises an eye to be inspected;
the optical tomographic apparatus further comprises an anterior ocular segment observing unit including a focus lens for anterior ocular segment observation, which observes an anterior ocular segment of the eye to be inspected and focuses to the anterior ocular segment; and the control unit causes the anterior ocular segment observing unit to focus to the anterior ocular segment in association with the change in the optical path length of the measuring light by the measuring light path length changing unit.

8. An optical tomographic apparatus according to claim 1, wherein the measuring light path length changing unit comprises an optical system moving mechanism for moving an optical system including an optical path of the measuring light with respect to the object to be inspected, and the control unit controls the reference light path length changing unit in association with the optical system moving mechanism, in accordance with the designation of the designating unit.

9. An optical tomographic apparatus according to claim 1, wherein the object to be inspected is an anterior ocular segment of an eye.

10. A method of controlling an optical tomographic apparatus configured to acquire a tomographic image of an object to be inspected based on light obtained by combining return light from the object to be inspected irradiated with measuring light with reference light corresponding to the measuring light, the method comprising the steps of:

receiving a designation relating to a size of an imaging area of the tomographic image; and controlling a reference light path length changing unit for changing an optical path length of the reference light, in association with a measuring light path length changing unit for changing an optical path length of the measuring light in accordance with the designation.

11. A method of controlling an optical tomographic apparatus according to claim 10, wherein the step of controlling comprises controlling, in accordance with the designation, the reference light path length changing unit in association with the measuring light path length changing unit, to change the optical path length of the reference light by a length corresponding to the change in the optical path length of the measuring light.

12. A method of controlling an optical tomographic apparatus according to claim 10, wherein the step of controlling comprising controlling, in accordance with the designation, the measuring light path length changing unit to change the optical path length of the measuring light by a length corresponding to a change of the designated size, and controlling the reference light path changing unit to change the optical path length of the reference light in association with the change in the optical path length of the measuring light.

13. A program for causing a computer to perform each step of the method of controlling an optical tomographic apparatus according to claim 10.

14. A method of controlling an optical tomographic apparatus according to claim 10, wherein the measuring light path length changing unit comprises an optical system moving mechanism for moving an optical system including an optical path of the measuring light with respect to the object to be inspected, and the step of controlling comprises controlling the reference light path length changing unit in association with the optical system moving mechanism, in accordance with the designation of the designating unit.

15. A method of controlling an optical tomographic apparatus according to claim 10, further comprising a step of displaying on a display a display form designating the change in the size of the imaging area of the tomographic image, and wherein the step of receiving comprises receiving the designation relating to the change in response to an operation of an operation unit.

* * * * *